United States Patent

Ciscato et al.

[11] Patent Number: 5,745,279
[45] Date of Patent: Apr. 28, 1998

[54] COLLIMATOR FOR RADIATION THERAPY

[75] Inventors: Doriano Ciscato; Aldo Rossi; Federico Colombo, all of Padova; Angiolino Grillini, S. Lazzaro Di Savena, all of Italy

[73] Assignee: Bassano Grimeca S.p.A., Ceregnano, Italy

[21] Appl. No.: 757,722

[22] Filed: Nov. 27, 1996

[30] Foreign Application Priority Data

Mar. 6, 1996 [IT] Italy .................. BO96A0116

[51] Int. Cl.⁶ ........................... G02B 26/02
[52] U.S. Cl. ............. 359/233; 359/230; 250/405.1; 250/491.1
[58] Field of Search ................. 359/233, 230, 359/223, 196; 250/396 R, 491.1, 505.1

[56] References Cited

U.S. PATENT DOCUMENTS

| | | | |
|---|---|---|---|
| 3,282,187 | 11/1966 | Cassidy et al. | 359/230 |
| 3,827,787 | 8/1974 | Ripart | 359/196 |
| 3,849,649 | 11/1974 | Carey | 359/233 |
| 3,871,750 | 3/1975 | Mecklenborg | 359/196 |
| 4,118,109 | 10/1978 | Crawford et al. | 359/196 |
| 4,220,866 | 9/1980 | Taumann | 250/513 |
| 4,581,515 | 4/1986 | Egashira | 359/233 |
| 4,850,686 | 7/1989 | Morimoto et al. | 359/196 |
| 4,869,583 | 9/1989 | Tiedje | 359/223 |
| 5,400,170 | 3/1995 | Hanada | 359/233 |

Primary Examiner—Georgia Y. Epps
Assistant Examiner—Thomas Robbins
Attorney, Agent, or Firm—Guido Modiano; Albert Josif

[57] ABSTRACT

A collimator for radiation therapy, particularly for medical use, including a first pair and a second pair of blocks for deflecting the radiation-therapy beam that is guided between the blocks of each pair, the pairs of blocks being superimposed with respect to each other and slidable on mutually perpendicular guides, a motor being provided to move the first and second pairs of blocks along the guides.

10 Claims, 2 Drawing Sheets

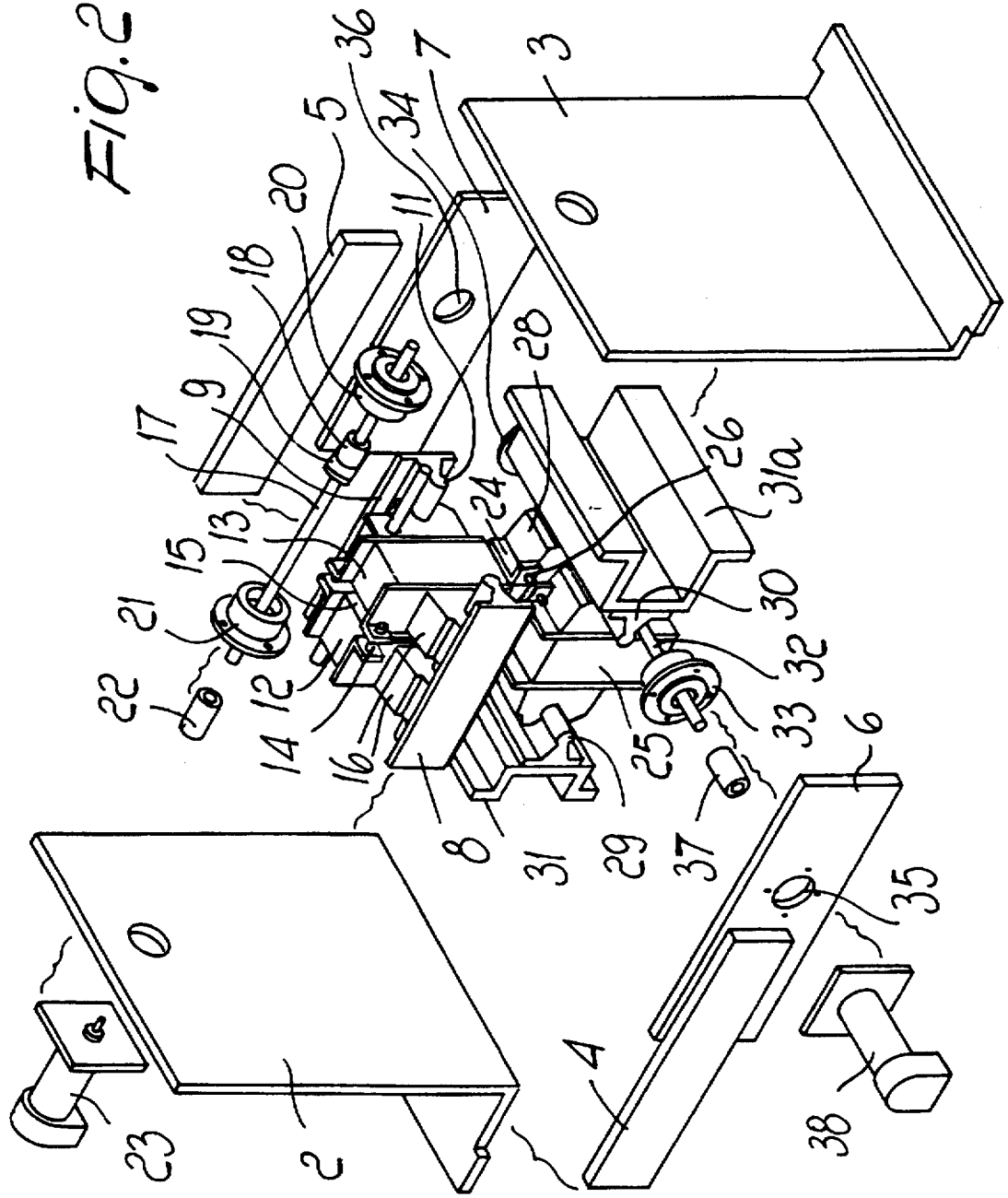

COLLIMATOR FOR RADIATION THERAPY

BACKGROUND OF THE INVENTION

The present invention relates to a collimator for radiation therapy. The invention is used mainly in the medical field to direct the radiation-therapy beam (beam of X rays) onto the intervention point.

Conventionally radiation therapy is performed in the medical field, particularly in the treatment of tumors. Since radiation therapy would have harmful effects on healthy tissues, it is highly important to provide exact aiming of the radiation-therapy beam only on the affected tissues, so as to prevent the beam from also acting on the healthy tissues, which must instead remain excluded from the therapy.

SUMMARY OF THE INVENTION

A principal aim of the present invention is therefore to provide a collimator that is capable of ensuring, with great exactness, that the radiation-therapy beam is trained on the intervention area.

Within the scope of this aim, an object of the present invention is to provide a collimator that can be robotized and programmed to allow deflections of the radiation-therapy beam within a certain region, so as to allow the therapeutic action of the beam without having to modify the position of the patient each time, which would otherwise require resetting the aiming parameters.

Another object of the present invention is to provide a device that is structurally simple and highly reliable in operation.

This aim, these objects and others which will become apparent hereinafter are achieved by a collimator for radiation therapy, particularly for medical use, characterized in that it comprises a first pair and a second pair of blocks for deflecting the radiation-therapy beam that is guided between the blocks of each pair, said pairs of blocks being superimposed with respect to each other and slidable on mutually perpendicular guides, motor means being provided to move said blocks along said guides.

BRIEF DESCRIPTION OF THE DRAWINGS

Further characteristics and advantages of the present invention will become apparent from the following detailed description of a preferred embodiment thereof, illustrated only by way of non-limitative example in the accompanying drawings, wherein:

FIG. 2 is an exploded view of the collimator of FIG. 1.

DESCRIPTION OF THE PREFERRED EMBODIMENTS

Figure 1:
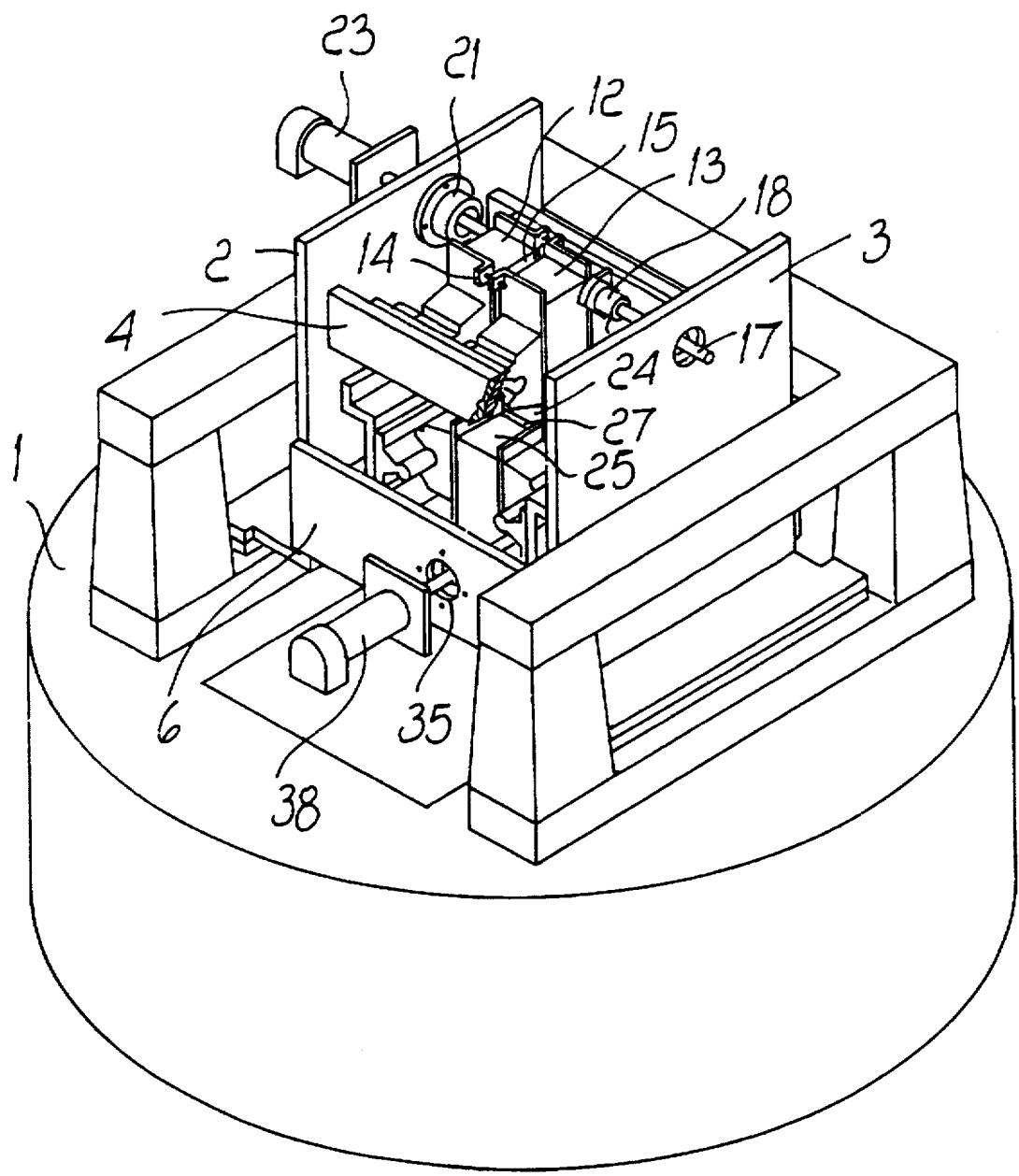
FIG. 1 is a perspective view of the collimator according to the present invention.

With reference to the above figures, the device comprises a base 1 from which two side walls 2 and 3 rise at right angles, said side walls being rigidly coupled to said base 1.

The side walls 2 and 3 are rigidly connected to each other at the top by two strips 4 and 5 and by two plates 6 and 7 at the bottom.

The strips 4 and 5 are located at the same level, and two portions 8 and 9 of a profiled element are fixed to their inner faces; said profiled element has a substantially T-shaped cross-section and comprises a ridge having a circular cross-section. The ridges constitute two respective guides 10 and 11 for two prism-shaped blocks 12 and 13 that are fixed, so as to be spaced from one another, by means of screws 14 so as to form a slit 15 through which the radiation-therapy beam, for example a beam of X rays, is guided. The blocks 12 and 13 are made of tungsten or copper or other material capable of deflecting the beam of X rays guided through the slit 15. The screws 14 are such as to allow to adjust the distance between the blocks 12 and 13 and therefore the width of the slit 15.

The blocks 12 and 13 rest slidingly on the guides 10 and 11 by means of sliders 16 (for the sake of clarity, only the sliders that can slide on the guide 10 are shown in the drawing) that have grooves that are complementary to the cross-section of the ridges constituting said guides and are such as to avoid excessive plays.

The blocks 12 and 13 can be moved along the guides 10 and 11 by means of a drive unit composed of a threaded rod 17 that engages, in a screw-like fashion, a female thread 18 that is provided with a flap 19 for fixing it to the side of the block 13.

The threaded rod 17 is rotatably supported in bushes 20 and 21 that are centered in holes of the side walls 2 and 3 and is rotationally coupled, by means of an elastic coupling 22, to the output shaft of a gearmotor or the like 23 that is coupled to the wall 2 by means of a flange. Two additional deflector blocks 24 and 25 are arranged below the blocks 12 and 13 and are coupled to each other by screws 26, so as to form, between them, a slit 27 lying on a plane that is perpendicular to the slit 15 of the overlying blocks 12 and 13.

The lower blocks 24 and 25 are also provided with sliders 28 that can slide on guides 29 and 30 which are fully identical to the guides 10 and 11 described above and are fixed to the side walls 2 and 3 by means of profiled elements 31 and 31a having an omega-shaped cross-section.

Movement of the blocks 24 and 25 along the guides 29 and 30 is provided by means of a threaded rod 32 that is rotatably supported in bushes 33 and 34 centered in holes 35 and 36 of the plates 6 and 7. A female thread (not shown in the drawings but fully identical to the one designated above by the reference numeral 18) is coupled to the rod 32, and the block 25 is connected to said female thread.

The rod 32 is motorized, by means of an elastic coupling 37, by a gearmotor 38 coupled to the plate 6 by means of a flange.

According to the above description, the slits 15 and 27, if viewed along the line where their planes of arrangement mutually intersect, form a gap through which the beam of X rays is projected. It is evident that by acting on the gearmotors 23 and 38 it is possible to move the upper blocks 12 and 13 with respect to the lower blocks and thus deflect the X-ray beam at the desired angle.

The independent movement of the deflector blocks 24,25 in mutually perpendicular directions is particularly advantageous; by allowing to deflect the beam of X rays at right angles, it allows to read its position in a reference system based on X-Y coordinates.

The described device is susceptible of numerous modifications and variations, all of which are within the scope of the same inventive concept.

For example, it is possible to use a ballscrew to move the blocks instead of using the threaded rod and the female thread.

In the practical embodiment of the invention, the shapes and dimensions may vary at will according to requirements.

What is claimed is:

1. A collimator for radiation therapy, particularly for medical use, comprising:
    an upper pair of deflecting blocks mutually arranged with respect to one another to define an upper slit extending in a first plane, said upper pair of deflecting blocks being adapted for deflecting a radiation-therapy beam so as to guide the beam in said upper slit;
    a lower pair of deflecting blocks mutually arranged with respect to one another to define a lower slit extending in a second plane, said lower pair of deflecting blocks being adapted for deflecting the radiation-therapy beam so as to guide the beam in said lower slit;
    a pair of mutually perpendicular guides upon a respective one of which a respective one of said pairs of deflecting blocks is slidably movable; and
    motor means for slidably moving said pairs of deflecting blocks along said guides;
    said upper pair of deflecting blocks being arranged above said lower pair of deflecting blocks such that a substantially linearly extending gap is defined extending through said upper slit and said lower slit in correspondence with an intersection of said first and second planes for directing said radiation-therapy beam through said linear gap.

2. A collimator according to claim 1, wherein each pair of deflecting blocks is slidingly guided on a respective one of said guides that are fixed to respective stationary side walls, a sliding movement of said blocks along said guides being provided by means of respective threaded rods that are rotatably supported in bushes centered in holes of said walls, each rod being coupled to a female thread that is connected to one of said blocks and being motorized, by means of an elastic coupling, by a gearmotor that is coupled to said wall by means of a flange.

3. A collimator according to claim 2, wherein said guides are constituted by profiled elements having a substantially T-shaped cross-section and having a ridge with a circular cross-section, whereon sliders are slidingly engaged, said sliders being fixed to said blocks and having grooves with a cross-section which is complementary shaped to a cross-section of said ridges.

4. A collimator according to claim 1, wherein each pair of deflecting blocks is slidingly guided on a respective one of said guides that are fixed to respective stationary side walls, a sliding movement of said blocks along said guides being provided by means of a ballscrew that is rotatably supported in bushes that are centered in holes of said walls and comprises a female thread connected to one of said blocks, said ballscrew being motorized, by means of an elastic coupling, by a gearmotor that is coupled to said side wall by means of a flange.

5. A collimator according to claim 4, wherein said guides are constituted by profiled elements having a substantially T-shaped cross-section and having a ridge with a circular cross-section, whereon sliders are slidingly engaged, said sliders being fixed to said blocks and having grooves with a cross-section which is complementary shaped to a cross-section of said ridges.

6. A collimator according to claim 1, wherein the blocks of each pair are interconnected by screw means that allow to adjust a distance between said blocks and the respective slit formed thereby.

7. A collimator according to claim 1 wherein said guides comprise:
    a first guide extending in a first linear direction for slidably guiding said upper pair of deflecting blocks along said first linear direction; and
    a second guide extending in a second linear direction for slidably guiding said lower pair of deflecting blocks along said second linear direction;
    said first linear direction being perpendicular to said second linear direction.

8. A collimator according to claim 7 wherein said first liner direction is perpendicular to said first plane and wherein said second linear direction is perpendicular to said second plane.

9. A collimator according to claim 8 wherein the blocks of said upper pair of deflecting blocks are mutually adjustably positionable for changing a width of said upper slit.

10. A collimator according to claim 9 wherein the blocks of said lower pair of deflecting blocks are mutually adjustably positionable for changing a width of said lower slit.

* * * * *